US005738996A

United States Patent [19]
Hodges et al.

[11] Patent Number: 5,738,996
[45] Date of Patent: Apr. 14, 1998

[54] COMBINATIONAL LIBRARY COMPOSITION AND METHOD

[75] Inventors: Robert S. Hodges, Edmonton; Randall T. Irvin, Sherwood Park, both of Canada; Arne Holm, Holte, Denmark; Wah Y. Wong, Edmonton, Canada; Hasmukh B. Sheth, Edmonton, Canada; Devon L. Husband, Edmonton, Canada

[73] Assignee: Pence, Inc., Edmonton, Canada

[21] Appl. No.: 260,199

[22] Filed: Jun. 15, 1994

[51] Int. Cl.$^6$ .................................................. G01N 33/53
[52] U.S. Cl. ..................... 435/7.1; 436/501; 436/518; 436/531; 436/543; 530/333; 530/334
[58] Field of Search ..................... 435/7.1, 6; 436/501, 436/518, 531, 543; 530/333, 334; 427/2.1, 211, 222

[56] References Cited

U.S. PATENT DOCUMENTS

| | | | |
|---|---|---|---|
| 4,963,263 | 10/1990 | Kauvar | 210/635 |
| 5,106,834 | 4/1992 | Bouy et al. | 514/15 |
| 5,182,366 | 1/1993 | Huebner et al. | 530/334 |
| 5,266,684 | 11/1993 | Rutter et al. | 530/334 |

FOREIGN PATENT DOCUMENTS

| | | |
|---|---|---|
| WO 86/00991 | 2/1986 | WIPO. |
| WO 92/09300 | 6/1992 | WIPO. |
| 9322684 | 11/1993 | WIPO. |

OTHER PUBLICATIONS

Zucerg, *Biochemistry*, Addison–Wesley Publishing Company, Inc. (1983), p. 143.

Furka, Árpád, et al., "General Method for Rapid Synthesis of Multicomponent Peptide Mixture," *Int. J. Peptide Protein Res.* 37:487–493 (1991).

Houghton, Richard A., et al., "Generation and Use of Synthetic Peptide Combinatorial Libraries for Basic Research and Drug Discovery," *Nature* 354:84 (1991).

Wong, Wah Y., et al., "Representative Combinatorial Peptide Libraries: An Approach to Reduce both Synthesis and Screening Efforts," *Methods in Enzymol.* 6:404–410 (1994).

Alper, J., "Drug Discovery on the Assembly Line," *Science* 264: 1399–1401 (1994).

Barbas, C.F. III, et al., "Semisynthetic combinatorial antibody libraries: A chemical solution to the diversity problem," *Proc. Natl. Acad. Sci. USA* 89: 4457–4461 (1992).

Brummel, C., et al., "A Mass Spectrometric Solution to the Address Problem of Combinatorial Libraries," *Science* 264: 399–402 (1994).

Dooley, C.T., et al., "Acetalins: Opioid receptor antagonists determined through the use of synthetic peptide combinatorial libraries," *Proc. Natl. Acad. Sci. USA* 90: 10811–10815 (1993).

Dooley, C.T., and R.A. Houghten, "The use of positional scanning synthetic peptide combinatorial libraries for the rapid determination of opioid receptor ligands," *Life Sciences* 52(18): 1509–1517 (1973).

Ecker, D.J., et al., "Rational screening of oligonucleotide combinatorial libraries for drug discovery," *Nucleic Acids Research* 21(8): 1853–1856 (1993).

Eichler, J., and R.A. Houghten, "Identification of Substrate-Analog Trypsin Inhibitors through the Screening of Synthetic Peptide Combinatorial Libraries," *Biochemistry* 32: 11035–11041 (1993).

Fodor, S.P.A., et al., "Light–Directed, Spatially Addressable Parallel Chemical Synthesis," *Science* 251: 767–773 (1991).

Houghten, R.A., et al., "Generation and use of synthetic peptide combinatorial libraries for basic research and drug discovery," *Nature* 354: 84–86 (1991).

Houghten, R.A., "Finding the needle in the haystack," *Current Biology* 4(6): 564–567 (1994).

Lam, K.S., et al., "A new type of synthetic peptide library for identifying ligand–binding activity," *Nature* 354: 82–84 (1991).

Lam, K.S., et al., "Discovery of D–amino–acid–containing ligands with selectide technology," *Gene* 137: 13–16 (1993).

Lam, K.S., and M. Legl, "Streptavidin and Avidin Recognize Peptide Ligands with Different Motifs," *Immunomethods* 1: 11–15 (1992).

Lam, K.S., "Treatment of B–cell Lymphoma Using Peptides," *The Western Journal of Medicine* 158(5): 475–479 (1993).

Needles, M.C., et al., "Generation and screening of an oligo–nucleotide–encoded synthetic peptide library," *Proc. Natl. Acad. Sci. USA* 90: 10700–10704 (1993).

Pinilla, C., et al., "Synthetic peptide combinatorial libraries (SPCLs): identification of the antigenic determinant of β–endorphin recognized by monoclonal antibody 3E7," *Gene* 138: 71–76 (1993).

*Primary Examiner*—Lora M. Green
*Attorney, Agent, or Firm*—Charles K. Sholtz; Peter J. Dehlinger

[57] ABSTRACT

A combinatorial library composition and method for using the library to construct oligomers effective to bind to a selected ligand is disclosed. The library composition includes at least two sets of ar oligomer libraries, each library set having selected oligomer subunit positions filled by known subunits, and other subunit positions containing permutations of subunits. In the selection method, oligomers from each library set are identified, and a new permutation library formed of subunits corresponding to the highest binding affinity oligomers in each library is screened for binding affinity to the selected ligand.

8 Claims, 10 Drawing Sheets

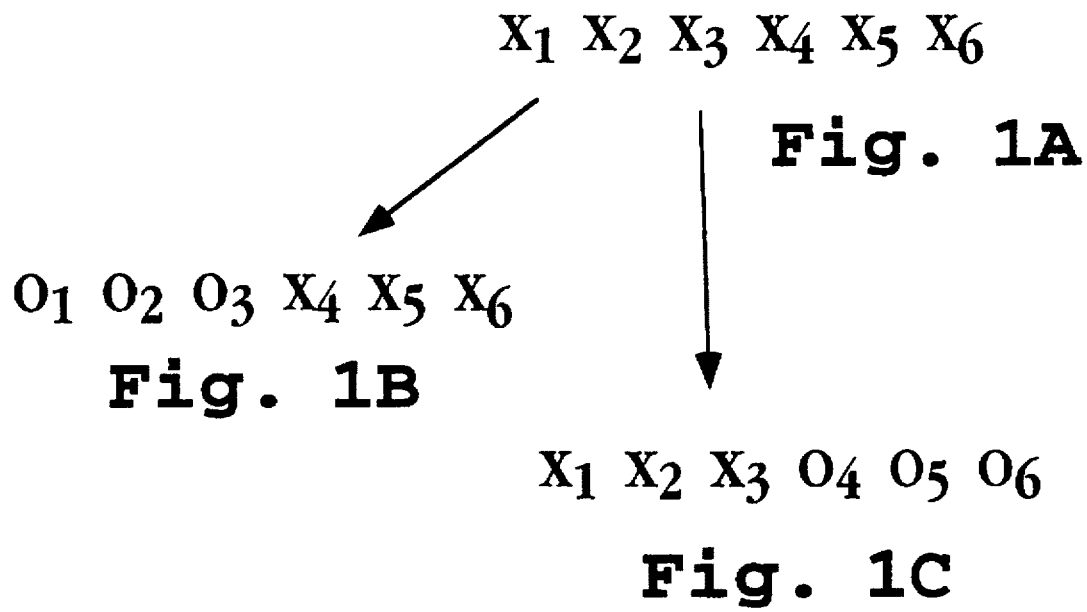

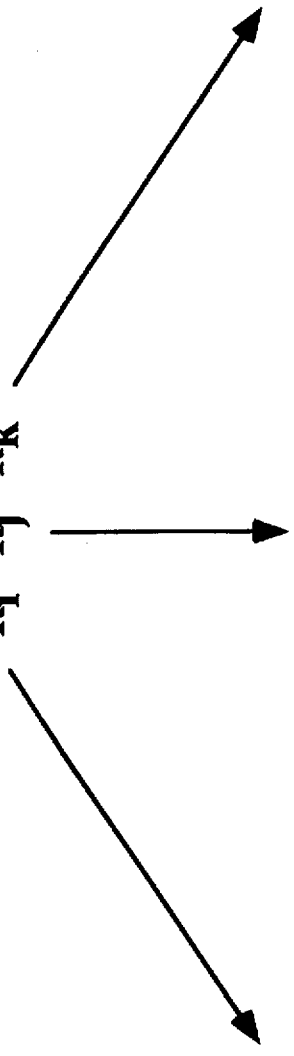

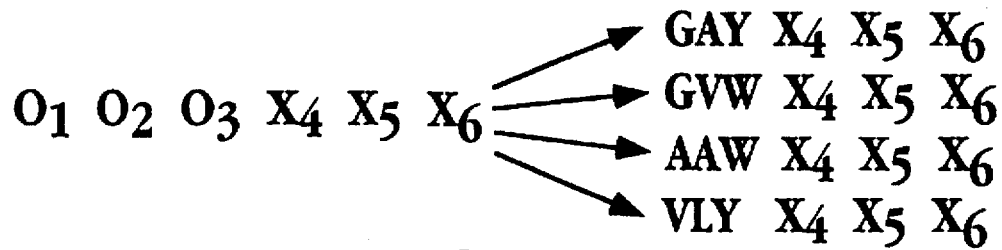
Fig. 6A
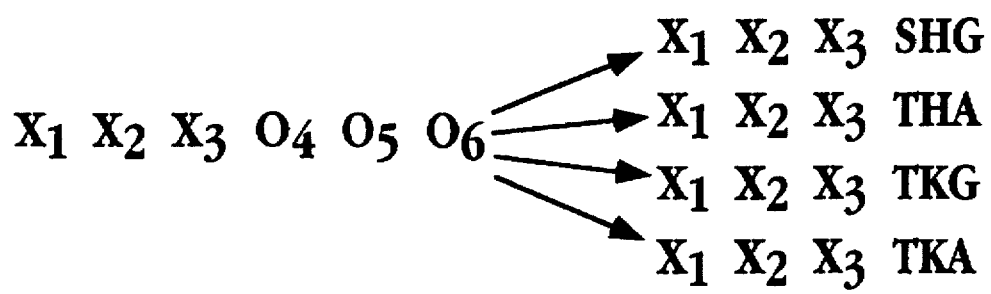
Fig. 6B
SEQ ID:31: GAY SHG
SEQ ID:32: GAY THA
⋮                    → AAWTKG (SEQ ID:34)
⋮
⋮                    → VLYSHG (SEQ ID:35)
SEQ ID:33: VLYTKA
Fig. 7

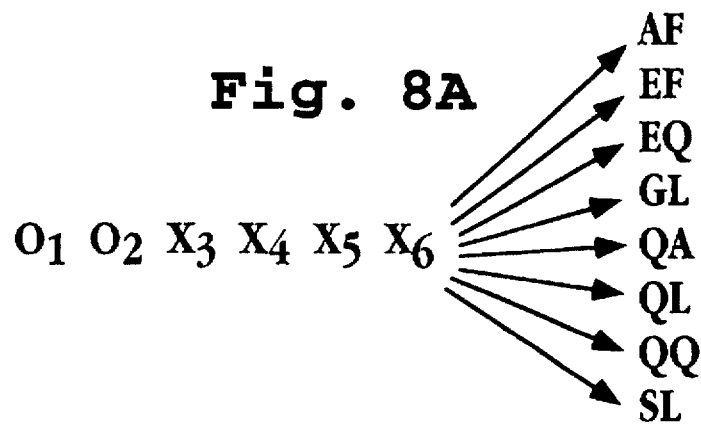

Fig. 8A $O_1\ O_2\ X_3\ X_4\ X_5\ X_6 \longrightarrow$ AF, EF, EQ, GL, QA, QL, QQ, SL $X_1\ X_2\ O_3\ O_4\ X_5\ X_6 \longrightarrow$ FI

Fig. 8B

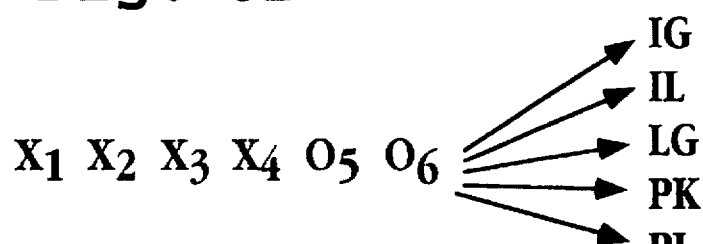

Fig. 8C $X_1\ X_2\ X_3\ X_4\ O_5\ O_6 \longrightarrow$ IG, IL, LG, PK, PL

SEQ ID:3: EQFIPK*
SEQ ID:4: QQFIPK*
SEQ ID:5: QAFIPK*
SEQ ID:6: AFFIPK
SEQ ID:7: GQFIPK
SEQ ID:8: EQFIIG

Fig. 9

SEQ ID:18: DQFIPK*
SEQ ID:19: ENFIPK
SEQ ID:20: EQYIPK
SEQ ID:21: EQWIPK*
SEQ ID:22: EQFMPK*
SEQ ID:23: EQFVPK*
SEQ ID:24: EQFIPH
SEQ ID:25: EQFIPR
SEQ ID:26: NQFIPK
SEQ ID:27: QNFIPK
SEQ ID:28: NAFIPK
SEQ ID:29: GNFIPK

Fig. 10

COMBINATIONAL LIBRARY COMPOSITION AND METHOD

1. FIELD OF THE INVENTION

The present invention relates to combinatorial peptide libraries, methods of screening such libraries and the identification of synthetic peptide antigens.

2. REFERENCES

Barbas, C. F., et al., *Proc. Natl. Acad. Sci. USA* 89(10):4457 (1992).

Blake, J., and Litzi-Davis, L., *Bioconjugate Chem.* 510–513 (1992).

Doig, P., et al., *Infect. Immun.* 58:124–130 (1990).

Dooley, C. T., et al., *Proc. Natl. Acad. Sci. USA* 90(22):10822 (1993a).

Dooley, C. T., et al., *Life Sci.* 52(18):1509 (1993b).

Ecker, D. J., et al., *Nuc. Acids Res.* 21(8):1853 (1993).

Eichler, J., et al., *Biochemistry* 32(41):11035 (1993).

Erickson, B. W., and Merrifield, R. B., in *The Proteins*, p. 255, Academic Press, Inc., New York (1976).

Fan, N., et al., *J. Clin. Micro.* 30(4):905 (1992).

Fields, G. B., and Noble, R. L., *Int. J. Peptide Protein Res.* 35:161–214 (1990).

Fodor, S. P. A., et al., *Science* 251:767–773 (1991).

Furka, A., et al., *14th Int'l Congress on Biochem.* 5:47 (Prague, Czechoslovakaia, July 10–15) (1988a).

Furka, A., et al., *14th Int'l Congress on Biochem.* 5:288 (Prague, Czechoslovakaia, August 15–19) (1988b).

Furka, A., et al., *Int. J. Pept. Protein Res.* 37:487–493 (1991).

Gausepohl, H., et al., *Peptide Res.* 5:315–320 (1992).

Geysen, H. M., et al., *Proc. Natl. Acad. Sci. USA* 81:3998–4002 (1984).

Geysen, H. M., et al., *Proc. Natl. Acad. Sci. USA* 82:178–182 (1985).

Hodges, R. S., et al., *Peptide Res.* 1:19–30 (1988).

Holm, A., and Meldal, M., "Multiple Column Peptide Synthesis" in *Peptides* 1988 (Bayer, et al., Eds., Walter deGruyter & Co., Berlin-New York) p. 208 (1989).

Hortin, G. L., et al., *Biochem. Int.* 26:731–738 (1992).

Houghten, R. A., *Proc. Natl. Acad. Sci. USA* 85:5131–5135 (1985).

Houghten, R. A., et al., *BioTechniques* 4:522–528 (1986).

Houghten, R. A., et al., *Nature* 354:84–86 (1991).

Houghten, R. A., et al., *BioTechniques* 13:412–421 (1992).

King, D. S., et al., *Int. J. Peptide Protein Res.* 36:255–266 (1990).

Kramer, A., et al., *Pept. Res.* 6(6):314 (1993).

Krichbaum-Stenger, K., et al., *Blood* 70:1303 (1987).

Meldal, M., et al., *Int. J. Peptide & Protein Res.* 41:250 (1993).

Ohlmayer, M. H., et al., *Proc. Natl. Acad. Sci. USA* 90:23:10922 (1993).

Pinilla, C., et al., *Biotechniques* 13(6):901 (1992).

Pinilla, C., et al., *Gene* 128(1):71 (1993).

Schulz, G. E. and R. H. Schirmer., *Principles of Protein Structure*, Springer-Verlag.

Schumacher, T. N. M., et al., *Eur. J. Immunol.* 22:1405–1412 (1992).

Sebestyen, F., et al., *Bioorg. Med. Chem. Lette* 3:413–418 (1993).

Wong, W. Y., et al., *Protein Sci.* 1:1308 (1992).

Zuckermann, R. N., et al., *Int. J. Pept. Protein Res.* 40:498–507 (1992).

3. BACKGROUND OF THE INVENTION

Currently there is widespread interest in using combinatorial libraries of random-sequence oligonucleotides, polypeptides, or synthetic oligomers to search for biologically active compounds (Kramer; Houghten, 1992, 1991; Ohlmayer; Dooley, 1993a–1993b; Eichler; Pinilla, 1993, 1992; Ecker; and Barbas). Ligands discovered by screening libraries of this type may be useful in mimicking or blocking natural ligands, or interfering with the naturally occurring interactions of a biological target. They can also provide a starting point for developing related molecules with more desirable properties, e.g., higher binding affinity.

Combinatorial libraries of the type useful in this general application may be formed by a variety of solution-phase or solid-phase methods in which mixtures of different subunits are added stepwise to growing oligomers, until a desired oligomer size is reached. A library of increasing complexity can be formed in this manner, for example, by pooling multiple choices of reagents with each additional subunit step (Houghten, 1991; 1993c).

Alternatively, the library may be formed by solid-phase synthetic methods in which beads containing different-sequence oligomers that form the library are alternately mixed and separated, with one of a selected number of subunits being added to each group of separated beads at each step. An advantage of this method is that each bead contains only one oligomer specie, allowing the beads themselves to be used for oligomer screening (Furka, 1991; Lam, 1991, 1993; Zuckermann; Sebestyen).

Still another approach that has been proposed involves the synthesis of a combinatorial library on spatially segregated arrays (Fodor). This approach is generally limited in the number of different library sequences that can be generated.

Since the chance of finding useful ligands increases with the size of the combinatorial library, it is desirable to generate libraries composed of large numbers of different-sequence oligomers. In the case of oligonucleotides, for example, a library having 4-base variability at 8 oligomer residue positions will contain as many as $4^8$ (65,536) different sequences. In the case of a polypeptides, a library having 20-amino acid variability at six residue positions will contain as many as $20^6$ (64,000,000) different species.

Because each different-sequence specie in a large-number library may be present in small amounts, one of the challenges in the combinatorial library selection procedure is isolating and determining the sequence of specie(s) that have the desired binding or other selected properties.

Where the combinatorial library consists of oligonucleotides, this problem may be solved by amplifying the isolated sequence, e.g., by polymerase chain reaction methods. In the case of polypeptide libraries, other methods must be employed. Where the library oligomers have been formed on beads, and each bead represents one polypeptide specie, it may be possible to conduct microscale sequencing on the oligomers contained on a single isolated bead. This approach, of course, is limited to selection procedures involving particles.

In another approach, where the library has been formed by pooling multiple choices of reagents during synthesis, a pool which is shown to have desired properties is resynthesized iteratively with lower and lower complexity until a single sequence compound is identified. This approach is not only relatively laborious, but tends to "screen out" subunit permutations that may be good candidates for high-affinity oligomers, but which are eliminated at early stages of iterative resynthesis in favor of one or a few higher-affinity oligomers.

Another basic consideration in the generation of desired compounds by screening combinatorial libraries is the nature of the selected compound itself. Polynucleotide libraries are relatively easy to generate and can be sequenced at low concentrations, but the structural variation within a library is limited by the relatively few bases that are employed, typically the standard four bases/oligomer position.

In the case of polypeptide libraries, these also can be synthesized readily by known solution or solid-phase methods, and the possibility of 20 (or more) different side chains at each oligomer position greatly expands the potential variability of the library. However, as indicated above, the large number of subunit permutations in a peptide combinatorial library composed of oligomers having 5 or more subunits sharply limits the amount of any one species available for sequence determination.

It would thus be desirable to provide a combinatorial library that retains a high potential for variability, yet can be readily manipulated to identify high-affinity binding species within the library. It is further desirable to be able to screen such a library in a solution phase, and identify likely candidates for high-binding affinity, but in a way that retains a significant number of possible subunits at each oligomer position, such that the "screening out" problem associated with reiterative resynthesis methods of sequence identification is avoided.

4. SUMMARY OF THE INVENTION

The invention includes, in one aspect, a method of generating an oligomer compound capable of interacting specifically with a selected receptor.

The method includes the steps of (a) reacting the receptor with each of a set of combinatorial oligomer libraries in which one or more selected subunit positions in the library oligomers have one of the different subunit permutations in each of the selected positions, and the remaining one or more subunit positions in each library include substantially all possible combinations of the different subunits, and (b) selecting from the set of libraries, one or more libraries which show an elevated level of interaction with the receptor, thereby identifying one or more high-affinity subunit compositions corresponding to the selected subunit positions.

Steps (a) and (b) above are repeated with another group of selected one or more subunit positions, until substantially all of the subunit positions in the libraries oligomers have been considered. The receptor is then reacted with a permutation library of oligomers formed of placing the highest-affinity compositions identified in the steps above in each of the associated oligomer positions. From this permutation library is selected one or more oligomers which show the greatest level of interaction with the receptor.

In one example, for use in selecting a hexapeptide oligomer having three N-terminal and three C-terminal positions, one set of combinatorial libraries contains a library for each of the possible permutations of amino acids in the three N-terminal positions, and a second set of combinatorial libraries contains a library for each of the possible permutations of amino acids in the three C-terminal positions.

In another example, for use in selecting a hexapeptide oligomer having two N-terminal, two intermediate, and two C-terminal positions, one set of combinatorial libraries contains a library for each of the possible permutations of amino acids in the two N-terminal positions, a second set of combinatorial libraries contains a library for each of the possible permutations of amino acids in the two intermediate positions, and a third set of combinatorial libraries contains a library for each of the possible permutations of amino acids in the two C-terminal positions.

In one general embodiment, for use in identifying a polypeptide oligomer capable of interacting specifically with a selected receptor, the subunits are representative amino acids that display the basic physico-chemical properties associated with naturally occurring amino acids, but exclude many of these naturally occurring amino acids. One group of representative amino acids include one from each of the groups (a) Ala, (b) Glu and Asp, (c) Phe, Tyr, and Trp, (d) Gly, (e) Ile and Val, (f) Lys, His, and Arg, (g) Leu, Met and Cys, (h) Pro, (i) Gln and Asn, and (j) Ser and Thr.

The method is also applicable for identifying oligomers having a large number of subunit possibilities at each oligomer position, e.g., up to 50 or more subunits, such as in a library of oligomers having an upstream subunit position, and intermediate subunit position, and a downstream subunit position, one or more of which may be single-subunit positions. In such an embodiment, the combinatorial libraries used in the method include a first set of libraries containing a combinatorial library for each of the possible subunits in the upstream subunit position, a second set of combinatorial libraries containing a library for each of the possible subunits in the intermediate subunit position, and a third set of combinatorial libraries containing a library for each of the possible subunits in the downstream subunit position.

In another aspect, the invention includes a combinatorial library composition for use in selecting an oligomer compound capable of interacting specifically with a selected macromolecular receptor.

The composition includes a first set of combinatorial oligomer libraries in which one or more selected subunit positions in the library oligomers have one of substantially all possible different subunits in each of the selected positions, and the remaining one or more subunit positions in each library include substantially all possible combinations of the different subunits, and a second set of combinatorial oligomer libraries in which one or more different selected subunit positions in the library oligomers have one of substantially all possible different subunits in each of the selected positions, and the remaining one or more subunit positions in each library include substantially all possible combinations of the different subunits.

As one example, for use in selecting a hexapeptide oligomer having three N-terminal and three C-terminal positions, the first set of combinatorial libraries contains a library for each of the possible permutations of amino acids in the three N-terminal positions, and the second set of combinatorial libraries contains a library for each of the possible permutations of amino acids in the three C-terminal positions.

As another example, for use in selecting a hexapeptide oligomer having two N-terminal, two intermediate, and two C-terminal positions, the first set of combinatorial libraries contains a library for each of the possible permutations of amino acids in the two N-terminal positions, and the second set of combinatorial libraries contains a library for each of the possible permutations of amino acids in the two intermediate positions. The composition further includes a third set of combinatorial libraries containing a library for each of the possible permutations of amino acids in the two C-terminal positions.

In one general embodiment, for use in identifying a polypeptide oligomer capable of interacting specifically with a selected receptor, the subunits are representative amino acids that display the basic physico-chemical properties associated with naturally occurring amino acids, such as described above.

In another general embodiment, the composition is designed for identifying oligomers having a large number of subunit possibilities at each oligomer position, e.g., up to 50 or more subunits, such as in a library of oligomers having an upstream subunit position, and intermediate subunit position, and a downstream subunit position, one or more of which may be single-subunit positions.

In this embodiment, the composition includes a first set of libraries containing a combinatorial library for each of the possible subunits in the upstream subunit position, a second set of combinatorial libraries containing a library for each of the possible subunits in the intermediate subunit position, and a third set combinatorial libraries containing a library for each of the possible subunits in the downstream subunit position.

The method and composition above have been used to construct novel antigens that are immunoreactive with antibodies directed against certain pathogenic bacterial and fungal organisms. The novel antigens, which form yet another aspect of the invention, are identified by SEQ ID NOS:3, 4, 5, 18, 21, 22, and 23. These and other objects and features of the invention will be more fully appreciated when the following detailed description of the invention is read in conjunction with the accompanying drawings.

BRIEF DESCRIPTION OF THE FIGURES

FIGS. 1A–1C are representations of combinatorial libraries of hexamers having different subunits $X_i$ at positions 1–6 (FIG. 1A), and two complementary sets of libraries (FIGS. 1B and 1C) formed in accordance with the invention;

FIGS. 2A and 2B show representative peptide combinatorial libraries corresponding to those represented in FIGS. 1B and 1C, respectively;

FIGS. 3A–3D are representations of a combinatorial library of hexamers having different subunits $X_i$ at positions 1–6 (FIG. 3A), and three complementary sets of libraries (FIGS. 3B–3D) formed in accordance with the invention;

FIGS. 4A–4C show representative peptide combinatorial libraries corresponding to those represented in FIGS. 3B–3D, respectively;

FIGS. 5A–5D are representations of a combinatorial library of trimers having different subunits $S_i$ at positions 1–3 (FIG. 5A), and three complementary sets of libraries (FIGS. 5B–5D) formed in accordance with the invention;

FIGS. 6A and 6B illustrate the selection of four combinatorial libraries from each of two sets of complementary hexapeptide libraries such as those shown in FIGS. 2A and 2B;

FIG. 7 shows representative members of a permutation peptide library formed from the amino acid sequences selected in FIGS. 6A and 6B, and further selection of the permutation library;

FIGS. 8A–8C illustrate the selection of eight, one, and five combinatorial libraries, respectively, from each of three sets of complementary hexapeptide libraries such as those shown in FIGS. 4A–4C, respectively;

FIG. 9 shows representative members of a permutation peptide library formed from the amino acid sequences selected in FIGS. 8A–8C;

FIG. 10 shows representative members of another permutation peptide library having peptides including amino acids other than the "representative" amino acids used to construct the "reduced set" libraries in FIGS. 8A–8C;

DETAILED DESCRIPTION OF THE INVENTION

I. Definitions

Figure 11A:
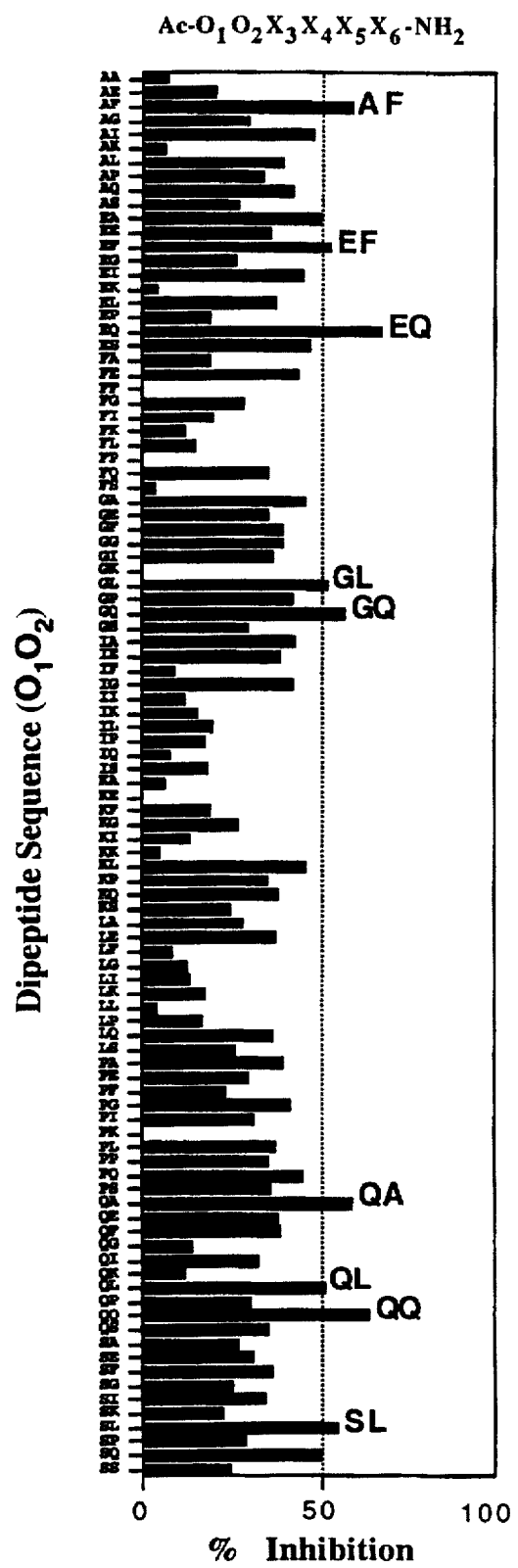
FIGS. 11A–11C show actual antibody binding data for the screening of the three sets of hexapeptide libraries indicated in FIGS. 8A–8C, respectively.

Unless otherwise indicated, all terms used herein have the same meaning given below:

An "oligomer" refers to a polymer composed of typically between about 3–12 subunits, where each subunit may be one of a plurality of different possible subunits.

A "combinatorial library of oligomers" refers to a library of oligomer molecules containing a large number, typically between 103 and 107 different-sequence oligomers, typically defined by a different sequence of subunits. Each sequence in a library is preferably represented by a plurality, e.g., $10^8$–$10^{12}$ molecules of the same sequence.

"Subunit position" in a combinatorial library of oligomers refers to the residue position of a subunit in a library of same-size oligomers. Where the oligomer is represented as a left-to-right linear string of subunits, the leftmost position will be designated as position 1, the position immediately to the right of position 1, as position 2, and so on.

"Permutations of different subunits" refers to known permutations of different subunits placed in selected oligomer positions. Thus, for example, several amino acid permutations of the first two positions in a oligopeptide include AlaAla, AlaArg, AlaAsn, AlaAsp, and so on.

"Combinations of different subunits" refers to random combinations of different subunits in selected oligomer positions, preferably including all or substantially all possible combinations of different subunits.

A "macromolecular receptor" or "receptor" is a macromolecule capable of specifically interacting with ligand molecules, including oligomers selected in accordance with the inventions. Binding of the ligand to the receptor is typically characterized by a high binding affinity, i.e., $K_b > 10^5$ mole$^{-1}$, and is intended to affect, e.g., inhibit, the function of the receptor in its normal biological setting. The receptor is also referred to herein as a target structure.

"Representative amino acids that display the basic physico-chemical properties associated with naturally occurring amino acids" refer to a set of amino acids that include at least one amino acid for each group of amino acids whose side chain(s) confer a selected size, hydrophobicity, charge, and/or structure-forming property on the amino acid, as described in Section II below. Abbreviations for amino acid residues are the standard 3-letter and/or 1-letter codes used in the art to refer to one of the 20 common L-amino acids.

II. Library Composition

This section describes a combinatorial library composition constructed in accordance with the invention.

The composition includes two or more sets of combinatorial oligomer libraries. In each set, one or more selected subunit positions have one of substantially all possible different subunits in each of the selected positions, and the remaining one or more subunit positions include substantially all possible combinations of the different subunits.

FIGS. 1A–1C illustrate a general a combinatorial library composition, where the oligomer is a hexamer, and the composition includes two library sets. The hexamer in FIG. 1A contains six subunits "X" at subunit positions 1–6. The subunits forming the oligomer may be, for example, amino acids in an oligopeptide, including standard and non-standard and derivatized L- and D-amino acids, amino acids coupled through non-amide linkages, forming an polypeptoid, nucleotides or trinucleotide codons in a polynucleotide, or other subunits based on ribose, glucose, or modified sugars with appropriate side chains or bases. Alternatively, the oligomer may be a molecular structure having a plurality of "subunit" R groups attached to the structure at designated positions on the structure, e.g., six different substitutions position on a parent cyclic structure.

For purposes of illustration, the library composition will be described with respect to a hexapeptide composition in which the allowed subunits include some or all of the standard 20 L-amino acids. The first library set, illustrated in FIG. 1B, is formed by filling each of the first three positions, indicated by $O_1$, $O_2$, and $O_3$, with each of the possible subunits. Each of the $O_1O_2O_3$ permutations will then form one library in the set, with the remaining positions $X_4$, $X_5$, and $X_6$ in each library preferably containing all or substantially all combinations of the different subunits placed in the subunits positions 4–6.

Representative members of this library set are shown in FIG. 2A, where each library contains one of the 8,000 possible three-subunit permutations in its first three position, such as permutations AAA, AAR, ARA, and so on to VVV. The last three positions, i.e., positions 4–6 in each of these 8,000 libraries, preferably contain all or substantially all of the 8,000 combinations of the different subunits. That is each library in a set includes a known sequence of subunits at positions 1–3, and a combinatorial library of sequences at positions 4–6.

The second set of libraries in the composition is shown at FIG. 1C. Each library in this set is formed by filling each of the last three positions, indicated by $O_4$, $O_5$, and $O_8$, with each of the possible subunits, with the remaining positions $X_1$, $X_2$, and $X_3$ in each library preferably containing all or substantially all combinations of the different subunits placed in subunit positions 1–3.

Representative members of this library set are shown in FIG. 2B, where each library contains one of the 8,000 possible three-subunit permutations in its last three position, such as permutations AAA, AAR, ARA, and so on to VVV. The first three positions, i.e., positions 1–3 in each of these 8,000 libraries preferably contain all or substantially all of the 8,000 combinations of the different subunits. That is, each library in a set includes a known sequence of subunits at positions 4–6, and a combinatorial library of sequences at positions 1–3.

The two library sets are complementary in that together, they include a combinatorial library for each of a known subunit permutation at positions 1–3 and 4–6.

In one preferred embodiment, which is useful for purposes of simplifying the synthesis and selection procedures in the method of the invention, the subunits forming the oligomers in the library composition are representative amino acids, typically including between about 8–12 amino acids that are representative of most of all of the commonly classified groups of amino acids, based on the physicochemical properties of the amino acids. These properties include the size, hydrophobicity, charge, and/or structure-forming properties that the side chains impart on the amino acid. Libraries generated using such a reduced set of representative amino acids are termed reduced combinatorial peptide libraries, or RCPLs.

One recognized grouping of amino acids by physicochemical properties includes the groups (a) Ala, representing a small, uncharged side chain; (b) Glu and Asp, representing negatively charged amino acids; (c) Phe, Tyr, and Trp, representing side chains with aromatic groups; (d) Gly, representing a very small side chain and one which confers high flexibility of backbone conformation, (e) Ile and Val, representing β-branched, hydrophobic side chains; (f) Lys, His, and Arg, representing positively charged amino acids; (g) Leu, Met, and Cys, representing large hydrophobic and sulfur-containing side chains; (h) Pro, representing a side chain with a strong influence on secondary structure, and in particular, on turns; (i) Gln and Asn, representing amide-containing side chains; and (j) Ser and Thr, representing hydroxyl-containing side chains.

One exemplary set of amino acids include the ten amino acids Ala (A) from group (a); Glu (E) from group (b); Phe (F) from group (c); Gly (G) from group (d); Ile (I) from group (e); Lys (K) from group (f); Leu (L) from group (g); Pro (P) from group (h); Gln (Q) from group (i); and Ser (S) from group (j).

As can be appreciated, this group of amino acids reduces the number of libraries in the three-position library sets described with reference to FIGS. 1 and 2 from 8,000 to 1,000 (10×10×10), and similarly reduces the number of combinations in each combinatorial library from 8,000 to 1,000. That is, each of the 1,000 libraries in each set includes now only 1,000 different sequences in positions 4–6, for the first library set, and at position 1–3, for the second library set.

s 3A–3D illustrate another general combinatorial library composition, where the oligomer is a hexamer, and the composition includes three library sets. The hexamer in FIG. 3A contains six subunits "X" at subunit positions 1–6. The subunits forming the oligomer may be, for example, any of the compositions described above in reference to FIGS. 1A–1C. One embodiment, described below, is comprised of three sets of hexapeptide libraries.

The first library set, illustrated in FIG. 3B, is formed by filling each of the first two positions, indicated by $O_1$ and $O_2$, with each of the possible subunits. Each of the $O_1O_2$ permutations will then form one library in the set, with the remaining positions $X_3$, $X_4$, $X_5$, and $X_6$ in each library preferably containing all or substantially all combinations of the different subunits placed in the subunits positions 3–6.

Representative members of this library set are shown in FIG. 4A, where each library contains one of the 400 possible two-subunit permutations in its first two position, such as permutations AA, AR, RA, and so on to VV. The last four positions, i.e., positions 3–6 in each of these 400 libraries preferably contain all or substantially all of the 160,000 combinations of the different subunits at positions 3–6. That is, each library in a set includes a known sequence of subunits at positions 1 and 2, and a combinatorial library of sequences at positions 3–6.

The second set of libraries in the composition is shown at FIG. 3C. Each library in this set is formed by filling the intermediate two positions, indicated by $O_3$ and $O_4$, with each of the possible subunits, with the remaining positions $X_1$, $X_2$, $X_5$, and $X_6$ in each library preferably containing all or substantially all combinations of the different subunits placed in subunit positions 3 and 4.

Representative members of this library set are shown in FIG. 4B. Each library contains one of the 400 possible two-subunit permutations in its intermediate two positions, and preferably all or substantially all of the 160,000 combinations of different subunits at positions 1, 2, 5, and 6.

Similarly, the third library set, shown in FIG. 3D includes 400 combinatorial libraries corresponding to known sequences in the fifth and sixth positions, and preferably all or substantially all of the 160,000 possible combinations in positions 1–4 of each of the libraries in the set, as illustrated in FIG. 4C.

The three library sets are complementary in that together, they include a combinatorial library for each of a known subunit permutation at positions (1, 2), (3,4), and (5,6).

Another type of combinatorial library composition includes oligomers composed of subunits in which the subunits may be, for example, backbone moieties, such as peptide or ribose, deoxyribose, or glucose, with a multiplicity (e.g., 20–100) R group side chains. Alternatively, the subunits may be, for example, a single parent molecule with three "R" positions, substituted at any of the three R positions. The R groups here may be any of a large number of common organic-compound radicals, such as alkyl groups, substituted alkyl groups, aryl groups, substituted aryl groups, and acid, aldehyde, amine, sulfhydryl, and alcohol groups, either alone or in combination with alkyl or aryl groups.

An example of this type of composition is illustrated in FIGS. 5A–5D. In this case, the oligomer is a trimer (FIG. 5A), which contains three subunits "S" at subunit positions 1–3, where $S_1$ has one of a plurality of possible R groups, indicated by $R_i$, subunit $S_2$ carries one of a plurality of R groups indicated by $R_j$, and so forth.

The first library set, illustrated in FIG. 5B, is formed by placing at the $R_i$ position, each of n different R groups. Each subunit $S_1$ having a different R group will then form one library in the set, with the remaining subunits in each library preferably containing all or substantially all combinations of the different R groups for $R_k$. That is, the composition includes N libraries which have a known R group in the first position and are combinatorial in the second and third positions.

Similarly, a second set of n combinatorial libraries will have n different known R group at the $R_j$ positions and be combinatorial in $R_i$, $R_k$, as shown in FIG. 5C, and similarly for a third set, shown in FIG. 5D.

The three library sets are complementary in that together, they include a combinatorial library for each of a known subunit R-group permutation at positions 1, 2 and 3.

III. Construction of Libraries

This section describes the synthesis of a composition of library sets, as described above, in which the subunits are peptides formed by a representative group of L-amino acids.

As noted above, both solution-phase and solid-phase synthetic methods may be employed. In one general embodiment for producing one of the libraries in a library set, the solid-phase resin used in the method is reacted with either a mixture of subunits, at the "combinatorial" subunit positions, or with a known monomer or dimer subunit, at the "known" subunit positions.

By way of example, to prepare a library set of 100 combinatorial hexapeptide libraries (using 10 representative amino acids only), in which the first two positions are known, and the remaining four positions are combinatorial, one would distribute resin into 100 different reaction wells, and form the 100 different permutations of amino acids at the first two subunits formed on the resin. Thereafter, each reaction well would be reacted stepwise with a mixture of the 10 different subunits, effectively placing each of the possible subunits at the third position in each of the 100 libraries. This latter reaction involving a mixture of all amino acids is then repeated for the fourth, fifth, and sixth subunits positions, to form the desired library set. The general reaction chemistry may follow standard methods (e.g., Holm, Meldal)

A second library set having known subunit positions in the third and fourth position is similarly formed by first carrying our the first and second coupling reactions with amino acid mixtures in a single vessel, carrying out the third and fourth coupling reactions in 100 separate wells with different known combinations of two subunits in each well, and the fifth and sixth reactions with the amino acid mixtures again, but in the separate wells. The final library set with known permutations of amino acids at the fifth and sixth positions is similarly formed, carrying out the first four position additions in a single vessel with amino acid mixtures, and the final two additions in separate wells.

In another general approach, in which combinatorial libraries are formed in discrete substrates, such as pins, the different pins could contain each library of a set. Thus, each of the three library sets just described could be formed on a set of 100 pins, again employing known solid-phase coupling methods (Geysen, 1984; Geysen, 1985).

The general approach outlined above was followed to construct three sets of combinatorial libraries for hexapeptides constructed of ten representative amino acids, as detailed n Example 1. Synthesis of the library sets was on NovaSyn PR 500 resin (Novabiochem, La Jolla, Calif.), using Fmoc amino acid Pfp-esters (Novabiochem) and OtBu (Glu), tBu (Ser) and tBoc (Lys) side-chain protecting groups, as detailed in Example 1. Other resins amenable for use on an MCPSI include Rink-AM resin (Aminotech, Nepean, ON, Canada) and Benzhydrylamine resin (Bachem, Torrance, Calif. ).

At the known (selected) subunit positions in each peptide mixture, a 10 fold excess of the Fmoc amino acid Pfp-esters in DMF was used. At random positions, a mixture of 0.1 equivalent of each of the 10 Fmoc amino acid Pfp-esters in DMF was used.

It will be appreciated that the synthesis strategies described below for forming a peptide-library composition are applicable as well to library sets formed of nucleotides or other subunits, following conventional solution-phase or solid-phase synthetic methods for those different subunits.

Similarly, if the library sets are formed by substitution of different R groups on a parent structure, as described with reference to FIGS. 5A–5D, the synthetic scheme for selectively placing R groups at each of the different substitution positions may employ orthogonal protection groups, allowing deprotection and substitution at each position successively. Suitable orthogonal protection groups, and methods for deprotecting them for R-group coupling, are well known.

IV. Method of Selecting High-Affinity Oligomers

This section describes the method of the invention for generating an oligomer compound capable of interacting specifically with a selected macromolecular receptor, employing the combinatorial library composition described in Section II above.

In the method, each library in the library set is screened for its ability to interact specifically with a selected receptor, typically a macromolecular receptor. This reaction is typically a binding reaction, as measured by the formation of a binding complex between the receptor and one or more molecules in the library being screened.

The receptor is any biological receptor of interest, that is, one for which it is desired to identify an oligomer (ligand) that binds specifically to the receptor, to affect the functioning of the receptor in its normal physiological setting.

For example, the receptor may be an enzyme, where the oligomer is able to bind to the active site of the enzyme or otherwise inhibit or affect the action of the enzyme on a normal substrate.

In another general embodiment, the receptor may be a cell receptor protein, such as an ion channel or other transport receptor protein, or a receptor site for a hormone or other cell effector, or a receptor site for binding of pathogenic bacteria or viruses to a cell surface. The receptor protein may be associated with isolated cells with culture cells, with biological membrane particles isolated from tissues, with cells which are transformed to produce the receptor recombinantly, or with isolated cell receptors. Receptor proteins of this type, and expressed or isolated in a variety of forms, have been described in the literature, such as that cited above.

In a related embodiment, the receptor is an antibody or antibody fragment, where it is desired to identify an "artificial" epitope ligand that binds specifically and with high affinity to the antibody.

Figure 12:
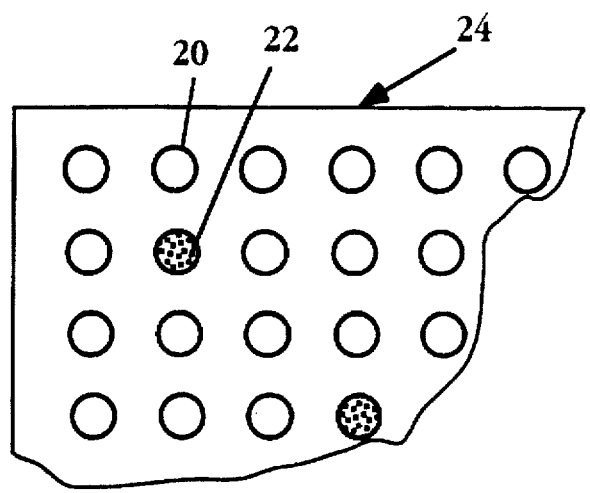
FIG. 12 shows a portion of a microtitre plate used in screening a library set in the invention.
Figure 13A:
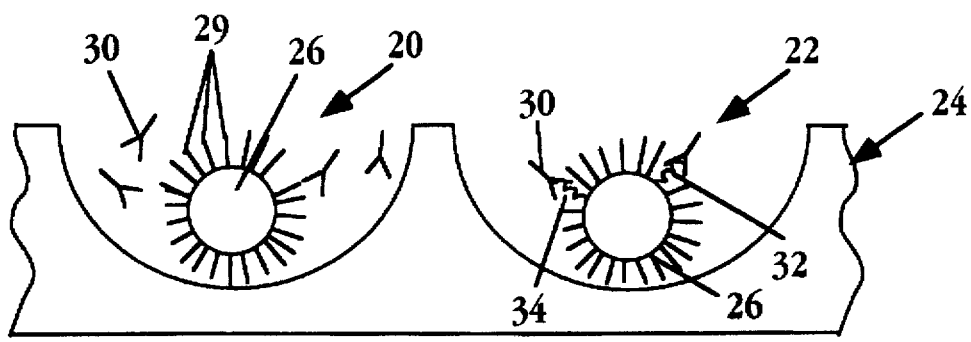
FIGS. 13A and 13B illustrate steps in one method for screening combinatorial libraries for the presence of oligomers having specific binding affinity for an antibody receptor.
Figure 13B:
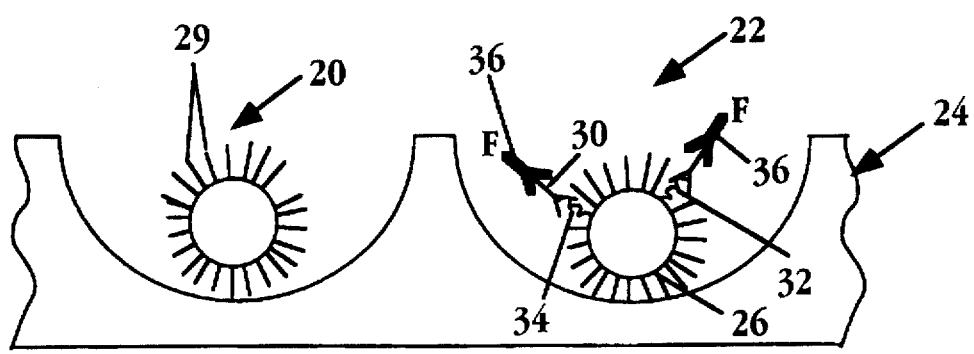

In a typical application, the library of oligomers is screened for oligomer (ligand) molecules that bind specifically and with high affinity, e.g., with a binding constant $K_B$ greater than $10^5 M^{-1}$, to the receptor. In one embodiment, illustrated in FIG. 12, each library is screened in one of the wells in a microtitre plate, such as wells 20, 22 in plate 24. FIGS. 13A and 13B show individual wells 10, 22 enlarged cross-sectional view. In the screening method, one of more resin particles of beads, such as bead 26, are placed in the wells, with each well containing one of the combinatorial libraries in a library set. That is, each bead in a selected well is coated with oligomers, such as those indicated at 29 on bead 26, representing an entire combinatorial library having fixed, known subunits in selected positions, e.g., the first two oligomer positions. Thus, in a 96-well microtitre plate, 96 libraries in a set of combinatorial can be screened.

After distributing each library in a set to one of the wells in a plate, the receptor, such as antibody receptor 30 in the figures is added each well, and the reaction mixtures are incubated under conditions that allow binding to library oligomers that show high-affinity with the receptor. In FIG. 13A, the library in well 20 carried on bead 26 does not contain such binding oligomers, and the antibody remains in solution. The library carried on bead 28 in well 22 does, however, have oligomers, indicated at 32, 34, which bind the antibody receptor, as indicated.

After this incubation step, the wells are washed to remove unbound material, and the beads in each well are then incubated with a reporter-labeled antibody, such as antibody 36, which receptor antibody with the receptor antibody. After removing the second-antibody reagent, the wells are then examined for the presence of reporter label, indicating that the bead(s) in a labeled well contain at least one oligomer that has high binding affinity for the receptor. This is seen in FIG. 12, where beads in well 22 are shown as being reported labeled.

Figure 14A:
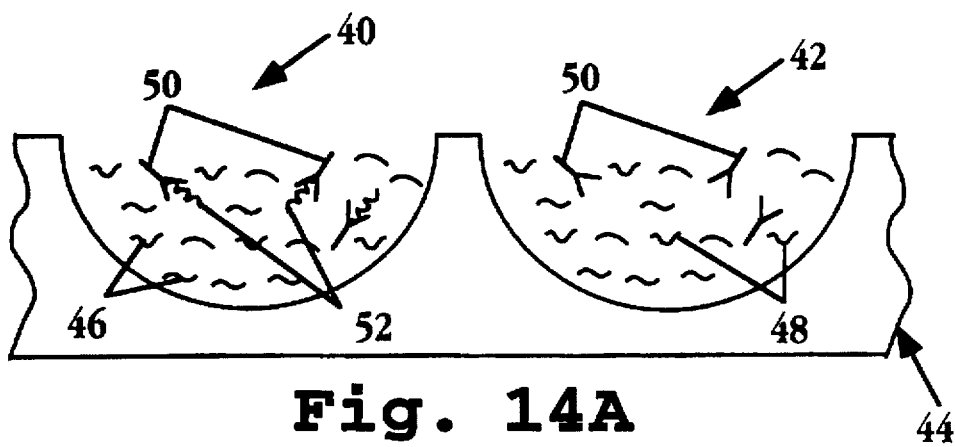
FIGS. 14A–14C illustrate steps in another method of screening libraries for the presence of oligomers having specific binding affinity for an antibody receptor.
Figure 14B:
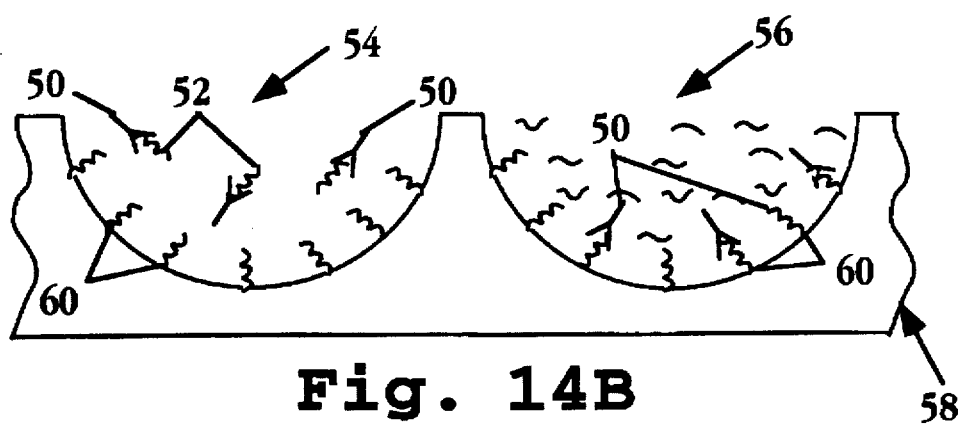
Figure 14C:
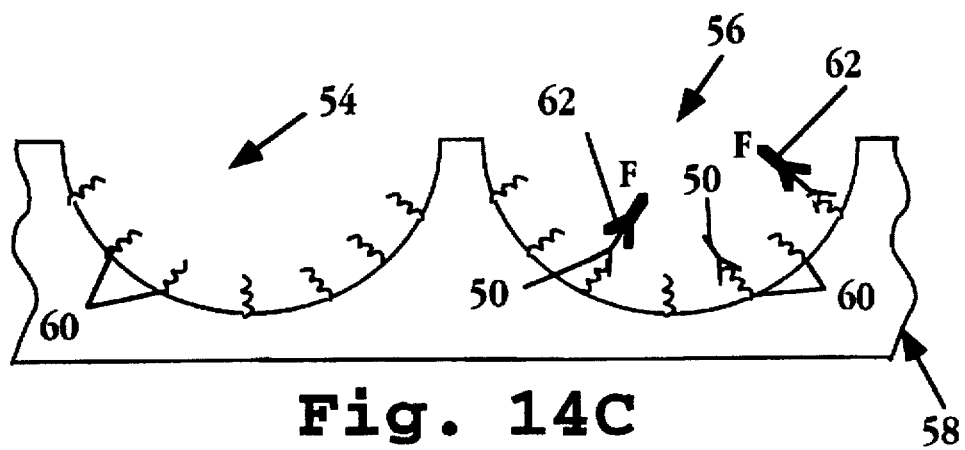

FIGS. 14A–14C illustrate another method for screening combinatorial libraries, in practicing the method of the invention. In this method, the combinatorial libraries in each set of libraries are screened in solution phase. The solution-phase libraries may be prepared, as above, with oligomer cleavage from a solid-phase resin following synthesis. FIG. 14A shows two wells 40, 42 in a microtitre plate used in the testing method. Each well in the plate, such as well 40, includes one of the combinatorial libraries to be tested, where each library is made up of oligomers having known subunits in selected subunit positions, and which are combinatorial in remaining positions, as described above. The library in well 40 is composed of oligomers, such as oligomers 46, and those in well 42, of oligomers, such as oligomers 48.

Each library is preincubated with a low molar concentration of an receptor, in this example, an antibody, as indicated at 50. The antibodies are immunoreactive with one or more oligomer species, such as indicated at 52, in the library in well 40, but not with the library in well 42.

The reaction mixture from each library is then added to a new well on a second plate, one library per well. As seen in FIG. 14B, the second wells, such as wells 54, 56 in plate 58, are each coated with antigen molecules, such as indicated at 60. These antigens are also immunoreactive with the receptor antibody. The added libraries are now allowed to react with the surface-bound antigen under conditions allowing immune complex formation between receptor antibody molecules are surface-bound antigen. As can be appreciated from FIGS. 14B, formation of an antibody-oligomer immunocomplex prevents antibody binding to the well surface (well 54). Conversely, in the absence of such complex formation, antibody becomes bound at maximum levels to the well surface (well 56).

Following this binding step, the wells are washed to remove unbound material, and reacted with reporter-labeled antibody, such as indicated at 62 in FIG. 14C. In wells containing bound receptor antibody, such as well 56 in FIG. 14C, the reporter-labeled antibody becomes bound to the well surface through the receptor antibody, as indicated. After washing the wells to remove unbound antibody, the wells are analyzed for the presence of bound reporter. The library or libraries in a set which are selected by this method are those that show low levels or the absence of bound reporter.

In the method of the invention, the screening steps just described are repeated for each of the library sets, e.g., the two sets of 1000-library sets described with respect to FIGS. 2A and 2B. For each set, one or more libraries showing high affinity binding to the receptor are identified. For example, in FIG. 6A, a first library set having known amino acid subunits in the first three positions is screened, and libraries having upstream-position sequences GAY, GVW, AAW, and VLY are identified as having high-affinity antigens. These results indicate that some of the combinatorial peptides having these upstream sequences are immunoreactive with the antibody receptor.

Similarly, the second library set is screened, and libraries having downstream-position sequences SHG, THA, TKG, and TKA are identified as having high-affinity antigens. These results indicate that some of the combinatorial peptides having these downstream sequences are immunoreactive with the antibody receptor.

Having identified in this manner, high-affinity subunits for all of the positions in the library oligomers, the next step in the method is to construct a permutation library of the high-affinity subunits. As an example, the four upstream and four downstream sequences identified in FIGS. 6A and 6B, respectively, can be combined to form 16 permutations, where the relative positions of the identified subunits are preserved.

That is, "high-affinity" upstream subunits are placed in upstream positions in the permutation oligomers, and "high-affinity" downstream subunits are placed in corresponding downstream positions. The resulting permutation library for the FIG. 6 sequence is shown in FIG. 7.

Each member of the permutation library is then tested to identify the highest affinity oligomers in the library. This may be done, for example, by determining the binding affinity of each library oligomer for the receptor, according to standard methods.

The method described above is illustrated in detail in Example 3, which describes a competitive ELISA screen of three complimentary sets of combinatorial libraries synthesized as detailed in Example 1. The libraries are of the form illustrated in FIGS. 3A–3D; that is, three sets of hexamer libraries with two "known" adjacent subunits (a dimer) in each set. The N-terminal set (HS1) has known residues at positions 1 and 2, as indicated in FIG. 3B by $O_1O_2$, the intermediate set (HS2) at positions 3 and 4 ($O_3O_4$), and the C-terminal at positions 5 and 6 ($O_5O_6$).

Combinatorial library sets HS1, HS2 and HS3 were initially screened for their ability to inhibit the interaction of a receptor, monoclonal antibody (Mab) PK99H, with its antigen (PAK peptide, SEQ ID NO:1). The antibody was generated as described in Example 2. It binds specifically to the C-terminal receptor binding domain of the PAK pilin protein (Doig, et al., 1990). The epitope recognized by PK99H consists of the hexapeptide sequence represented by SEQ ID NO:2 (Wong, 1992).

The antigen (PAK peptide, SEQ ID NO:1) was coated on the wells of an assay dish (96-well plate). The libraries in sets HS1, HS2 and HS3 were preincubated with PK99H to produce an immunocomplex between the antibody and any high-affinity library oligomers. The incubate was then added to a well on the plate, and further incubated under conditions sufficient to allow antibody binding to the surface-bound antigen.

Figure 11B:
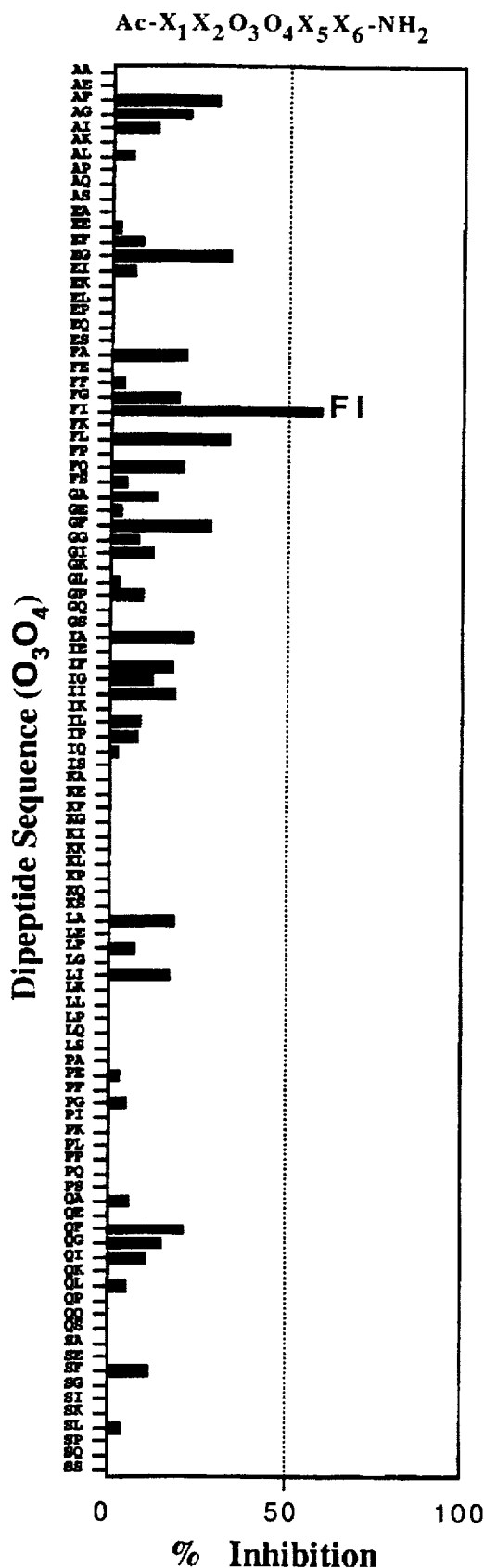
Figure 11C:
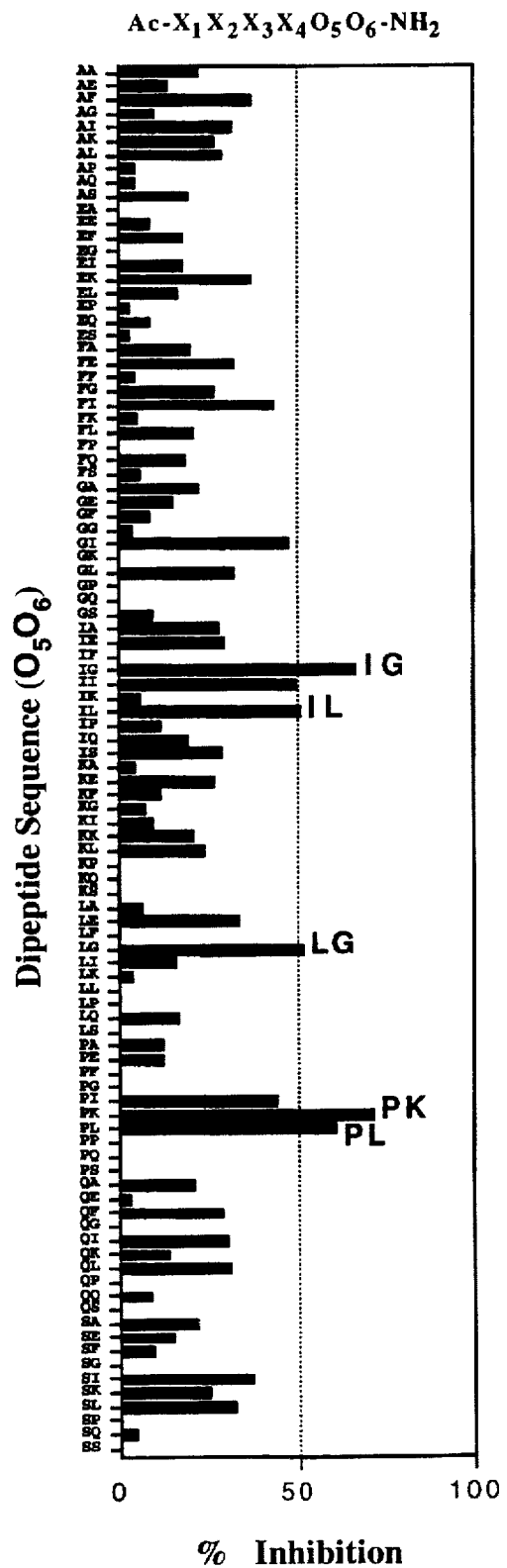

Example of the data from such a screen are illustrated in FIGS. 11A–11C. FIG. 11A shows the percent inhibition of PK99H binding to PAK (horizontal bars) obtained with HS1 libraries having the amino acids indicated along the y-axis at positions 1 and 2. The vertical, dotted line in the figure marks a level of 50% inhibition. Libraries resulting in a ≧50% inhibition of binding of PK99H to PAK peptide are scored as "hits", or "positives". The sequence at the first two positions of the positive libraries is indicated in bold to the right of the corresponding data bars.

Nine positive HS1 libraries were identified. The sequence at the first two positions (first dimer), in order of most inhibitory to least inhibitory, is EQ, QQ, QA, AF, GQ, SL, EF, GL and QL. A similar screen is performed with sets HS2 and HS3. The results are shown in FIGS. 11B and 11C, respectively. Only one positive HS2 library was identified, having the amino acids FI at positions 3 and 4 (second dimer), respectively. Five positive HS3 libraries are identified, having the sequences PK, IG, PL, LG and IL (in order of most inhibitory to least inhibitory) at positions 5 and 6 (third dimer).

A set of 15 permutation peptides was constructed, as above, using the five best dimer sequences identified in the screen of HS1 at the first dimer position, FI at the second dimer position and the three best HS3 dimer sequences at the third dimer position. The peptides were synthesized using the 10 representative amino acids indicated above, following the method detailed in Example 4.

Six of these peptides (indicated in Table 1) were soluble in aqueous medium, and were screened using a competitive ELISA, as detailed in Example 5. This assay is similar to that described above, and in Example 3, except that 10 mM, rather than 50 mM PBS is used during the incubations and the concentration of the hexapeptide being assayed is varied to construct a competitive binding curve from which $I_{50}$ values (the concentration of peptide required to produce a 50% inhibition of antibody binding to immobilized antigen) can be determined.

The results of the screen are shown in Table 1 as $I_{50}$ values for the six water-soluble peptides. The $I_{50}$ for the two most effective peptides is 1.3 μM. One of these, EQFIPK (SEQ ID NO:3) has a sequence that is contained in the sequence of the native epitope (SEQ ID NO:2). Interestingly, the sequence of EQFIPK corresponds to the dimer sequences identified as the most inhibitory in the screens of HS1, HS2 and HS3.

Two other permutation peptides, QQFIPK (SEQ ID NO:4) and QAFIPK (SEQ ID NO:5), have $I_{50}$ values similar to that of the native sequence (1.3 μM and 2.0 μM respectively). Peptides GQFIPK (SEQ ID NO:7) and EQFIIG (SEQ ID NO:8) show an 8-fold and 35-fold increase in $I_{50}$ values, respectively. One peptide, AFFIPK (SEQ ID NO:6), shows a large loss of inhibitory activity ($I_{50}$=1100 μM). The three peptides having $I_{50}$ values of 2 μM or less are identified by asterisk symbol in FIG. 9, and correspond to SEQ ID NOS: 3–5.

TABLE 1

| Peptide | SEQ ID NO.: | $I_{50}$ (μM) |
|---|---|---|
| EQFIPK | 3 | 1.3 |
| QQFIPK | 4 | 1.3 |
| QAFIPK | 5 | 2.0 |
| AFFIPK | 6 | 1100 |
| GQFIPK | 7 | 10 |
| EQFIIG | 8 | 45 |

To identify additional high-affinity binding compositions, the four highest-affinity permutation peptides identified above (SEQ ID NOs:3, 4, 5 and 7) are used as templates for the synthesis of variant permutation peptides having same-type amino acid substitutions at selected subunit positions. Twelve variants, identified by SEQ ID NOS: 18–29, were synthesized in a manner similar to the permutation peptides (detailed in Example 4), except that naturally-occurring amino acids other than the representative amino acids were used at certain selected subunit positions.

The strategy followed in the synthesis of the 12 variant permutation peptides is apparent from an examination of Table 2, which shows the sequences of the template peptides (SEQ ID NOS: 3, 4, 5, and 7) along with their respective variants peptides (SEQ ID NOS 18–29). The subunit positions substituted with same-type amino acids (selected form the 20 naturally occurring amino acids) are underlined in the sequences shown in Table 2.

The variant peptides were screened with a competitive ELISA as described above for the permutation peptides, and $I_{50}$ values are determined (data in Table 2). Two of the variant peptides (SEQ ID NOS:21 and 22) exhibit a higher degree of MAb PK99H antibody binding inhibition than the native sequence (0.9 μM and 1.1 μM, respectively).

TABLE 2

| Peptide | SEQ ID NO: | ID$_{50}$ (µM) |
|---|---|---|
| EQFIPK | 3 | 1.3 |
| DQFIPK | 18 | 2.3 |
| ENFIPK | 19 | 190 |
| EQYIPK | 20 | 190 |
| EQWIPK | 21 | 0.9 |
| EQFMPK | 22 | 1.1 |
| EQFVPK | 23 | 3.4 |
| EQFIPH | 24 | 620 |
| EQFIPR | 25 | >730 |
| QQFIPK | 4 | 1.3 |
| NQFIPK | 26 | 12 |
| QNFIPK | 27 | 990 |
| QAFIPK | 5 | 2.0 |
| NAFIPK | 28 | 14 |
| GQFIPK | 7 | 10 |
| GNFIPK | 29 | >840 |

It will be appreciated from the foregoing that other methods may be employed for selecting, from a set of combinatorial libraries, those libraries which show an elevated level of interaction with the ligand, in order to identify high-affinity subunit compositions.

One example is a screen based on the ability of library compositions of the present invention to inhibit the binding of a pathogen, such as a virus or bacterium, host cells. The host cells are isolated, for example, by "FICOLL-HYPAQUE" sedimentation, pelleted, resuspended in medium and incubated with a mixture of, for example, reporter-labelled virus (i.e. rhodamine-18-labeled virus; Fan, et al., 1992) that had been pre-incubated with a combinatorial library.

The cells are then washed, fixed, for example, with 1% paraformaldehyde, and the amount of bound virions determined by, for example, flow cytometric analysis. Libraries effective to reduce the binding of virus to the cells are identified as containing oligomers which bind with high affinity to a ligand (i.e. cell surface molecule) on the virus, and in so doing, block the binding of the virus to the cells.

From the foregoing, it will be appreciated how various objects and features of the invention are met. In practicing the method, the user is provided with typically two or three sets of combinatorial libraries. After screening the individual members of the library sets, one or more possible optimal subunits are identified for each subunit position. These identified subunits are then used to construct a relatively small number of permutations oligomers that can then be tested for optimal activity.

The method thus avoids the need to iteratively back synthesize new libraries at each successive screening stage, and therefore both faster and less expensive in terms of library constructs. The method also avoids "locking out" promising subunit possibilities occurs with iterative back synthesis, and thus more permutations of optimal combinations of subunits are preserved. This advantage can be appreciated from the peptides selected in Table 1 and 2 which show several high-affinity peptides produced by the method of the invention having alternative amino acid residues in each of the first four oligomer positions.

The following examples illustrate, but in no way are intended to limit the present invention.

MATERIALS AND METHODS

Abbreviations used: BSA, bovine serum albumin; DCM, dichloromethane; DMF, N,N-dimethylformamide; ELISA, enzyme-linked immunosorbent assay; Fmoc, 9-fluorenylmethoxycarbonyl; HPLC, high performance liquid chromatography; I$_{50}$, concentration of peptide required to produce 50% inhibition in competitive ELISA; MCPSI, Multiple Column Peptide Synthesis instrument; PAK, Pseudomonas aeruginosa strain K; PBS, phosphate-buffered saline; Pfp, pentafluorophenyl; RCPL, representative combinatorial peptide libraries; SPPS, solid-phase peptide synthesis; tBoc, tert-butyloxycarbonyl; tBu, tert-butyl; TFA, trifluoroacetic acid.

EXAMPLE 1

SYNTHESIS OF THE REPRESENTATIVE COMBINATORIAL PEPTIDE LIBRARIES

Peptide libraries were synthesized on NovaSyn PR 500 resin (0.3 mmol/g; Novabiochem, La Jolla, Calif.) for continuous flow synthesis of peptide amides, using a Multiple Column Peptide Synthesis Instrument (MCPSI). The physical layout and mechanical operation of the MCPSI has been previously described in detail by Holm et al. (Holm, et al., 1989; Meldal, et al., 1993). Briefly, the instrument is a manually operated apparatus for parallel solid-phase peptide synthesis. It is constructed with a Teflon reaction block with a 96-well (8×12) layout or a 100 well (10×10) layout. Each well resembles a column in the continuous flow version of the polyamide peptide synthesis method. Two washers are installed for dispensing of solvents and deprotecting reagents in a parallel fashion. Activated and protected amino acids are transferred from a dispenser tray as solutions, eight at a time Nitrogen gas was used to maintain a positive pressure in the chamber.

To each well, 20 mg of the resin was added. Fmoc amino acid Pfp-esters (Novabiochem, la Jolla, Calif.) were used for the synthesis. The side-chain protecting groups used were: OtBu (Glu), tBu (Ser) and tBoc (Lys). For those defined positions ($O_nO_{n+1}$) in each peptide mixture, 0.3M (10 folds excess) of the Fmoc amino acid Pfp-esters in DMF (200 µl/well) were used. Double couplings were performed for 2 hr and 30 min, respectively. In the case of X$_n$ position, a mixture of 0.1 equivalent of each of the 10 Fmoc amino acid Pfp-esters in DMF were used and coupled for 2 hr, followed by a second coupling for an additional 2 hr. Fmoc deprotection was carried out with 20% piperidine in DMF, and acetylation of the a-amino group was performed with excess acetic anhydride. The peptides were cleaved from the resin with 95% TFA/water (4×300 µl). The TFA solution was then evaporated to dryness using a Savant "SPEEDVAC" (Savant Instruments Inc., Farmingdale, N.Y.). The semi-solid products were washed three times with diethyl ether and then dried cautiously with a slow stream of nitrogen. The peptides were dissolved in water and centrifuged, the supernatant was transferred into a cryo-tube (Nunc, Denmark).

The synthesis was repeated until all libraries were synthesized. The peptide libraries were stored in lyophilized form.

EXAMPLE 2

PRODUCTION OF MONOCLONAL ANTIBODY PK99H

The monoclonal antibody, PK99H, was prepared as described by Doig, et al. (Doig, et al., 1990). Ascites tumors were produced by injecting 10$^6$ hybridoma cells into pristine primed BALB/c male mice. Ascites fluid was collected and partial purification was accomplished with ammonium sulfate fractionation and subsequently dialyzed against phosphate buffered saline (PBS), pH 7.4. Antibody was then purified by HPLC on a protein G affinity column (Chromato-Chem, Missoula, Mont.). PK99H is an IgG subclass 1 with k light chains.

EXAMPLE 3

COMPETITIVE ELISA SCREEN OF PEPTIDE LIBRARY

The peptide libraries were screened by competitive ELISA (Enzyme Linked Immunosorbent Assay) in 96-well microtiter plates purchased from Costar Corp. (Cambridge, Mass.). Microtiter plates from several other suppliers were also evaluated, but did not work as well with the peptide-antigen system described herein.

A microtiter plate was coated with the intrachain disulfide-bridged (oxidized) *Pseudomonas aeruginosa* strain K (PAK) 17-residue peptide (SEQ ID NO:1, 200 μM, 80 μl/well) in 0.01M carbonate buffer, pH 9.5. This peptide antigen corresponds to the C-terminal region of the PAK pilin.

The plate was incubated for 6 hr at room temperature and was subsequently blocked with 3% bovine serum albumin (BSA) in PBS at 4° C. overnight. Peptide library solutions (final concentration: 8 mM) were preincubated for an hour with the monoclonal antibody PK99H (250 μg protein/ml in stock solution, final dilution in each well was $2\times10^{-2}$ of the stock solution) in 50 mM PBS containing 0.05% BSA, pH 7.4 (incubation buffer). The solution mixtures (80 μl) were added into corresponding wells and incubated for two hours at 37° C. The plate was washed five times with the incubation buffer.

The amount of antibody bound was detected by goat anti-mouse IgG conjugated to horseradish peroxidase (Jackson Laboratories, Calif.) using 2,2'-azino-di-(3-ethylbenzthiazoline sulfonic acid) as a substrate. The substrate solution was prepared in 10 mM sodium citrate buffer, pH 4.2, containing 0.03% (v/v) hydrogen peroxide. The reaction was stopped by 4 mM sodium azide, and the absorbance was measured at 405 nm by a Titertek Multiskan Plus MK II microplate reader (Flow Lab Inc., McLean, Va.).

EXAMPLE 4

PEPTIDE SYNTHESIS

The synthesis was performed following the general procedure for solid phase synthesis as described by Erickson and Merrifield (Erickson and Merrifield, 1976) with modifications made by Hodges, et al. (Hodges, et al., 1988) on an Applied Biosystems 430A solid phase peptide synthesizer (Foster City, Calif.). All amino acids used were protected at the α-amino position with the tert-butyloxycarbonyl (tBoc-) group (Bachem Inc., Philadelphia, Pa.). Syntheses of peptide amides were carried out using co-poly (styrene, 1% divinylbenzene) benzhydrylamine-hydrochloride resin at a substitution of 0.92 mmol amino groups/g of resin (Bachem Inc., Philadelphia, Pa.). All amino acids were double coupled using dicyclohexylcarbodiimide generated symmetric anhydrides in DMF for the first coupling and dichloromethane (DCM) in the second coupling. Final acetylation was performed on the instrument using acetic anhydride.

After synthesis, peptides were cleaved from the resin support with anhydrous hydrogen fluoride (20 ml/g of peptide resin) in the presence of 10% (v/v) anisole and 1% (v/v) 1,2-ethanedithiol as scavenging reagents for 1 hour at −4° C. using type 1B HF-Reaction Apparatus (Peninsula Laboratories Inc., Belmont, Calif.). The solvent mixture was then removed under reduced pressure. The resin was washed with anhydrous diethyl ether (3×25 ml), and peptide was extracted with neat acetic acid (3×25 ml). The peptide solution was diluted with distilled water and then lyophilized.

Purification of crude peptides was performed by reversed-phase HPLC on an Applied Biosystems 400 solvent delivery system and a 783A programmable absorbance detector connected to a Synchropak RP-4 (250×21.2 mm I.D.) reversed-phase column (Synchrom Inc., Lafayette, Id.) using a linear AB gradient of 0.2% B/min at a flow rate of 5 ml/min, where solvent A was 0.05% TFA/water and solvent B was 0.05% TFA/acetonitrile. The absorbance was recorded at 210 nm. The purity and authenticity of the peptides were examined by means of analytical HPLC, amino acid analysis, and mass spectrometry. Analytical HPLC was done on an Aquapore RP-300, $C_8$ reversed-phase column (220×4.6 mm I.D., Brownlee Labs, Santa Clara, Calif.). Purified peptides were hydrolyzed with 6N HCl with 0.1% phenol in sealed, evacuated tubes at 110° C. for 22 hours, and amino acid analyses were performed on a Beckman System 6300 High Performance Automatic Analyzer (Beckman, Palo Alto, Calif.). The molecular weight and purity of the peptide was confirmed with a Biolon 20 Plasma Desorption Time of Flight mass spectrometer (Uppsala, Sweden).

EXAMPLE 5

COMPETITIVE ELISA SCREEN OF INDIVIDUAL PEPTIDES

Competitive ELISA was performed to determine the ability of the hexapeptides synthesized in inhibiting antibody binding to the peptide antigen. The assay was similar to the one detailed in Example 3, except that conventional 10 mM PBS was used instead of 50 mM PBS, and concentrations of the hexapeptides used during the incubation were varied.

This enabled the construction of a competitive binding curve from which $I_{50}$ values could be determined. The $I_{50}$ values were calculated using the software TableCurve (Jandel Scientific Inc., Calif.).

While the invention has been described with reference to specific methods and embodiments, it will be appreciated that various modifications and changes may be made without departing from the invention.

It is claimed:

1. For use in selecting an oligomer compound capable of interacting specifically with a selected macromolecular ligand, a combinatorial library composition comprising a first set of combinatorial oligomer libraries in which one or more selected subunit positions in the library oligomers have one of substantially all possible different subunits in each of the selected positions, and the remaining one or more subunit positions in each library include substantially all possible combinations of the different subunits, and a second set of combinatorial oligomer libraries in which one or more different selected subunit positions in the library oligomers have one of substantially all possible different subunits in each of the selected positions, and the remaining one or more subunit positions in each library include substantially all possible combinations of the different subunits, wherein the subunits are representative amino acids that display the basic physico-chemical properties associated with naturally occurring amino acids, but exclude many of these naturally occurring amino acids.

2. The composition of claim 1, wherein the subunits include at least one from each of the groups consisting of (a) Ala, (b) Glu and Asp, (c) Phe, Tyr, and Trp, (d) Gly, (e) Ile and Val, (f) Lys, His, and Arg, (g) Leu, Met, and Cys (h) Pro, (i) Gln and Asn, and (j) Ser and Thr.

3. The composition of claim 1, for use in selecting a hexapeptide oligomer having three N-terminal and three C-terminal positions, wherein the first set of combinatorial libraries contains a library for each of the possible permutations of amino acids in the three N-terminal positions, and the second set of combinatorial libraries contains a library for each of the possible permutations of amino acids in the three C-terminal positions.

4. The composition of claim 3, wherein the subunits include at least one from each of the groups consisting of (a) Ala, (b) Glu and Asp, (c) Phe, Tyr, and Trp, (d) Gly, (e) Ile and Val, (f) Lys, His, and Arg, (g) Leu, Met, and Cys (h) Pro, (i) Gln and Asn, and (j) Ser and Thr, and each of said sets of libraries includes between about 500–2,000 libraries.

5. The composition of claim 1, for use in selecting a hexapeptide oligomer having two N-terminal, two intermediate, and two C-terminal positions, wherein the first set of combinatorial libraries contains a library for each of the possible permutations of amino acids in the two N-terminal positions, and the second set of combinatorial libraries contains a library for each of the possible permutations of amino acids in the two intermediate positions, and which further includes a third set of combinatorial libraries contains a library for each of the possible permutations of amino acids in the two C-terminal positions.

6. The composition of claim 5, wherein the subunits include at least one from each of the groups consisting of (a) Ala, (b) Glu and Asp, (c) Phe, Tyr, and Trp, (d) Gly, (e) Ile and Val, (f) Lys, His, and Arg, (g) Leu, Met, and Cys (h) Pro, (i) Gln and Ash, and (j) Ser and Thr.

7. The composition of claim 1, for use in identifying a oligomer having an upstream subunit position, and intermediate subunit position, and a downstream subunit position, where each subunit can be filled with substantially more than 20 different subunits, wherein the first set of combinatorial libraries contains a library for each of the possible subunits in the upstream subunit position and the second set of combinatorial libraries contains a library for each of the possible subunits in the intermediate subunit position, and which further includes a third set of combinatorial libraries contains a library for each of the possible subunits in the downstream subunit position.

8. The composition of claim 7, wherein each subunit position can be filled by at least about 50 different subunits.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide (iii) HYPOTHETICAL: NO (iv) ANTI-SENSE: NO (vi) ORIGINAL SOURCE:
  (C) INDIVIDUAL ISOLATE: Pseudomonas aeruginosa strain K
  (PAK) peptide (xi) SEQUENCE DESCRIPTION: SEQ ID NO:1:

Lys Cys Thr Ser Asp Gln Asp Glu Gln Phe Ile Pro Lys Gly Cys Ser
1               5                   10                  15
Lys (2) INFORMATION FOR SEQ ID NO:2:

(i) SEQUENCE CHARACTERISTICS:
    (A) LENGTH: 7 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: MAb PK99H epitope peptide (xi) SEQUENCE DESCRIPTION: SEQ ID NO:2:

Asp Glu Gln Phe Ile Pro Lys
1               5

(2) INFORMATION FOR SEQ ID NO:3:

(i) SEQUENCE CHARACTERISTICS:
    (A) LENGTH: 6 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: EQFIPK peptide (xi) SEQUENCE DESCRIPTION: SEQ ID NO:3:

Glu Gln Phe Ile Pro Lys
1               5

(2) INFORMATION FOR SEQ ID NO:4:

(i) SEQUENCE CHARACTERISTICS:
    (A) LENGTH: 6 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: QQFIPK peptide . 14

(xi) SEQUENCE DESCRIPTION: SEQ ID NO:4:

Gln Gln Phe Ile Pro Lys
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: QAFIPK peptide . 14

( x i ) SEQUENCE DESCRIPTION: SEQ ID NO:5:

Gln Ala Phe Ile Pro Lys
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: AFFIPK peptide . 14

( x i ) SEQUENCE DESCRIPTION: SEQ ID NO:6:

Ala Phe Phe Ile Pro Lys
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: GQFIPK peptide . 14

( x i ) SEQUENCE DESCRIPTION: SEQ ID NO:7:

Gly Gln Phe Ile Pro Lys
1               5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
                    ( C ) INDIVIDUAL ISOLATE: EQFIIG peptide ( x i ) SEQUENCE DESCRIPTION: SEQ ID NO:8:

Glu Gln Phe Ile Ile Gly
        1               5

( 2 ) INFORMATION FOR SEQ ID NO:9:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
                    ( C ) INDIVIDUAL ISOLATE: QQFIIG peptide, . 14

( x i ) SEQUENCE DESCRIPTION: SEQ ID NO:9:

Gln Gln Phe Ile Ile Gly
        1               5

( 2 ) INFORMATION FOR SEQ ID NO:10:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
                    ( C ) INDIVIDUAL ISOLATE: QAFIIG peptide, . 14

( x i ) SEQUENCE DESCRIPTION: SEQ ID NO:10:

Gln Ala Phe Ile Ile Gly
        1               5

( 2 ) INFORMATION FOR SEQ ID NO:11:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
                    ( C ) INDIVIDUAL ISOLATE: AFFIIG peptide, . 14

( x i ) SEQUENCE DESCRIPTION: SEQ ID NO:11:

Ala Phe Phe Ile Ile Gly
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: GQFIIG peptide, . 14

( x i ) SEQUENCE DESCRIPTION: SEQ ID NO:12:

Gly Gln Phe Ile Ile Gly
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: EQFIPL peptide, . 14

( x i ) SEQUENCE DESCRIPTION: SEQ ID NO:13:

Glu Gln Phe Ile Pro Leu
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: QQFIPL peptide, . 14

( x i ) SEQUENCE DESCRIPTION: SEQ ID NO:14:

Gln Gln Phe Ile Pro Leu
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid (  C  ) STRANDEDNESS: single
                (  D  ) TOPOLOGY: unknown (  i i  ) MOLECULE TYPE: peptide (  i i i  ) HYPOTHETICAL: NO (  i v  ) ANTI-SENSE: NO (  v i  ) ORIGINAL SOURCE:
                (  C  ) INDIVIDUAL ISOLATE: QAFIPL peptide, . 14

(  x i  ) SEQUENCE DESCRIPTION: SEQ ID NO:15:

Gln  Ala  Phe  Ile  Pro  Leu
        1                  5

( 2 ) INFORMATION FOR SEQ ID NO:16:

(  i  ) SEQUENCE CHARACTERISTICS:
                (  A  ) LENGTH: 6 amino acids
                (  B  ) TYPE: amino acid
                (  C  ) STRANDEDNESS: single
                (  D  ) TOPOLOGY: unknown (  i i  ) MOLECULE TYPE: peptide (  i i i  ) HYPOTHETICAL: NO (  i v  ) ANTI-SENSE: NO (  v i  ) ORIGINAL SOURCE:
                (  C  ) INDIVIDUAL ISOLATE: AFFIPL peptide, . 14

(  x i  ) SEQUENCE DESCRIPTION: SEQ ID NO:16:

Ala  Phe  Phe  Ile  Pro  Leu
        1                  5

( 2 ) INFORMATION FOR SEQ ID NO:17:

(  i  ) SEQUENCE CHARACTERISTICS:
                (  A  ) LENGTH: 6 amino acids
                (  B  ) TYPE: amino acid
                (  C  ) STRANDEDNESS: single
                (  D  ) TOPOLOGY: unknown (  i i  ) MOLECULE TYPE: peptide (  i i i  ) HYPOTHETICAL: NO (  i v  ) ANTI-SENSE: NO (  v i  ) ORIGINAL SOURCE:
                (  C  ) INDIVIDUAL ISOLATE: GQFIPL peptide, . 14

(  x i  ) SEQUENCE DESCRIPTION: SEQ ID NO:17:

Gly  Gln  Phe  Ile  Pro  Leu
        1                  5

( 2 ) INFORMATION FOR SEQ ID NO:18:

(  i  ) SEQUENCE CHARACTERISTICS:
                (  A  ) LENGTH: 6 amino acids
                (  B  ) TYPE: amino acid
                (  C  ) STRANDEDNESS: single
                (  D  ) TOPOLOGY: unknown (  i i  ) MOLECULE TYPE: peptide (  i i i  ) HYPOTHETICAL: NO (  i v  ) ANTI-SENSE: NO (  v i  ) ORIGINAL SOURCE:
                (  C  ) INDIVIDUAL ISOLATE: DQFIPK peptide, . 15

( x i ) SEQUENCE DESCRIPTION: SEQ ID NO:18:

Asp Gln Phe Ile Pro Lys
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: ENFIPK peptide, . 15

( x i ) SEQUENCE DESCRIPTION: SEQ ID NO:19:

Glu Asn Phe Ile Pro Lys
1               5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: EQYIPK peptide, . 15

( x i ) SEQUENCE DESCRIPTION: SEQ ID NO:20:

Glu Gln Tyr Ile Pro Lys
1               5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: EQWIPK peptide, . 15

( x i ) SEQUENCE DESCRIPTION: SEQ ID NO:21:

Glu Gln Trp Ile Pro Lys
1               5

( 2 ) INFORMATION FOR SEQ ID NO:22:

( i ) SEQUENCE CHARACTERISTICS:
        ( A ) LENGTH: 6 amino acids ( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: EQFMPK peptide, . 15

( x i ) SEQUENCE DESCRIPTION: SEQ ID NO:22:

Glu Gln Phe Met Pro Lys
1               5

( 2 ) INFORMATION FOR SEQ ID NO:23:

( i ) SEQUENCE CHARACTERISTICS:
( A ) LENGTH: 6 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: EQFVPK peptide, . 15

( x i ) SEQUENCE DESCRIPTION: SEQ ID NO:23:

Glu Gln Phe Val Pro Lys
1               5

( 2 ) INFORMATION FOR SEQ ID NO:24:

( i ) SEQUENCE CHARACTERISTICS:
( A ) LENGTH: 6 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: EQFIPH peptide, . 15

( x i ) SEQUENCE DESCRIPTION: SEQ ID NO:24:

Glu Gln Phe Ile Pro His
1               5

( 2 ) INFORMATION FOR SEQ ID NO:25:

( i ) SEQUENCE CHARACTERISTICS:
( A ) LENGTH: 6 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:

(C) INDIVIDUAL ISOLATE: EQFIPR peptide, . 15

(x i) SEQUENCE DESCRIPTION: SEQ ID NO:25:

Glu Gln Phe Ile Pro Arg
1               5

(2) INFORMATION FOR SEQ ID NO:26:

(i) SEQUENCE CHARACTERISTICS:
      (A) LENGTH: 6 amino acids
      (B) TYPE: amino acid
      (C) STRANDEDNESS: single
      (D) TOPOLOGY: unknown (i i) MOLECULE TYPE: peptide (i i i) HYPOTHETICAL: NO (i v) ANTI-SENSE: NO (v i) ORIGINAL SOURCE:
      (C) INDIVIDUAL ISOLATE: NQFIPK peptide, . 15

(x i) SEQUENCE DESCRIPTION: SEQ ID NO:26:

Asn Gln Phe Ile Pro Lys
1               5

(2) INFORMATION FOR SEQ ID NO:27:

(i) SEQUENCE CHARACTERISTICS:
      (A) LENGTH: 6 amino acids
      (B) TYPE: amino acid
      (C) STRANDEDNESS: single
      (D) TOPOLOGY: unknown (i i) MOLECULE TYPE: peptide (i i i) HYPOTHETICAL: NO (i v) ANTI-SENSE: NO (v i) ORIGINAL SOURCE:
      (C) INDIVIDUAL ISOLATE: QNFIPK peptide, . 15

(x i) SEQUENCE DESCRIPTION: SEQ ID NO:27:

Gln Asn Phe Ile Pro Lys
1               5

(2) INFORMATION FOR SEQ ID NO:28:

(i) SEQUENCE CHARACTERISTICS:
      (A) LENGTH: 6 amino acids
      (B) TYPE: amino acid
      (C) STRANDEDNESS: single
      (D) TOPOLOGY: unknown (i i) MOLECULE TYPE: peptide (i i i) HYPOTHETICAL: NO (i v) ANTI-SENSE: NO (v i) ORIGINAL SOURCE:
      (C) INDIVIDUAL ISOLATE: NAFIPK peptide, . 15

(x i) SEQUENCE DESCRIPTION: SEQ ID NO:28:

Asn Ala Phe Ile Pro Lys
1               5

(2) INFORMATION FOR SEQ ID NO:29:

(i) SEQUENCE CHARACTERISTICS:

(A) LENGTH: 6 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: GNFIPK peptide, .15

(xi) SEQUENCE DESCRIPTION: SEQ ID NO:29:

Gly Asn Phe Ile Pro Lys
1               5

(2) INFORMATION FOR SEQ ID NO:30:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: FIPK peptide (xi) SEQUENCE DESCRIPTION: SEQ ID NO:30:

Phe Ile Pro Lys
1

(2) INFORMATION FOR SEQ ID NO:31:

(i) SEQUENCE CHARACTERISTICS:
(A) LENGTH: 6 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: GAYSHG peptide, .7

(xi) SEQUENCE DESCRIPTION: SEQ ID NO:31:

Gly Ala Tyr Ser His Gly
1               5

(2) INFORMATION FOR SEQ ID NO:32:

(i) SEQUENCE CHARACTERISTICS:
(A) LENGTH: 6 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: GAYTHA peptide, . 7

(xi) SEQUENCE DESCRIPTION: SEQ ID NO:32:

Gly  Ala  Tyr  Thr  His  Ala
    1                   5

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: VLYTKA peptide, . 7

(xi) SEQUENCE DESCRIPTION: SEQ ID NO:33:

Val  Leu  Tyr  Thr  Lys  Ala
    1                   5

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: AAWTKG peptide, . 7

(xi) SEQUENCE DESCRIPTION: SEQ ID NO:34:

Ala  Ala  Trp  Thr  Lys  Gly
    1                   5

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: VLYSHG peptide, . 7

(xi) SEQUENCE DESCRIPTION: SEQ ID NO:35:

Val  Leu  Tyr  Ser  His  Gly
    1                   5